(12) United States Patent
Carstens et al.

(10) Patent No.: US 9,416,095 B2
(45) Date of Patent: Aug. 16, 2016

(54) SALTS, CRYSTALS, COMPLEXES, AND DERIVATIVES OF THREONINE DIACETIC ACID, A PROCESS TO PREPARE THREONINE DIACETIC ACID, AND THE USE THEREOF

(71) Applicant: Akzo Nobel Chemicals International B.V., Arnhem (NL)

(72) Inventors: Axel Carstens, Kleve (DE); Tjerk Oedse Boonstra, Duiven (NL); Alexey Borisovich Zaitsev, Deventer (NL); Martin Heus, Arnhem (NL); Wouter Jan Veenis, Ede (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 14/905,432

(22) PCT Filed: Jul. 11, 2014

(86) PCT No.: PCT/EP2014/064894
§ 371 (c)(1),
(2) Date: Jan. 15, 2016

(87) PCT Pub. No.: WO2015/007630
PCT Pub. Date: Jan. 22, 2015

(65) Prior Publication Data
US 2016/0159730 A1 Jun. 9, 2016

(30) Foreign Application Priority Data
Jul. 16, 2013 (EP) ..................................... 13176649

(51) Int. Cl.
| C07C 227/18 | (2006.01) |
| C07C 229/16 | (2006.01) |
| C07C 253/00 | (2006.01) |
| C11D 3/33 | (2006.01) |

(52) U.S. Cl.
CPC ............. *C07C 227/18* (2013.01); *C07C 229/16* (2013.01); *C07C 253/00* (2013.01); *C11D 3/33* (2013.01)

(58) Field of Classification Search
None
See application file for complete search history.

(56) References Cited

U.S. PATENT DOCUMENTS

| 5,019,296 A | 5/1991 | Baur et al. |
| 5,521,056 A | 5/1996 | Buchanan et al. |
| 2011/0257431 A1 | 10/2011 | Baumann et al. |

FOREIGN PATENT DOCUMENTS

| EP | 0599620 A1 | 6/1994 |
| EP | 0624821 A1 | 11/1994 |
| EP | 0723194 A1 | 7/1996 |
| EP | 1004571 A1 | 5/2000 |
| EP | 2388308 A1 | 11/2011 |
| EP | 2086923 B1 | 8/2012 |
| JP | 11-021584 A | 1/1999 |
| JP | 11-021585 A | 1/1999 |
| JP | 11-092436 A | 4/1999 |
| JP | 2000008081 A | 1/2000 |
| JP | 2000026890 A | 1/2000 |
| JP | 2001-342453 A | 12/2001 |
| JP | 2002020792 A | 1/2002 |
| JP | 2002-287307 A | 10/2002 |
| JP | 2002-296745 A | 10/2002 |
| JP | 2004-204055 A | 7/2004 |
| JP | 2009-218473 A | 9/2009 |
| WO | 03/022406 A1 | 3/2003 |
| WO | 2005/095673 A1 | 10/2005 |
| WO | 2011/144699 A1 | 11/2011 |
| WO | 2011/154875 A1 | 12/2011 |

OTHER PUBLICATIONS

European Search Report for EP 13176649.5, date Nov. 25, 2013.

*Primary Examiner* — Yate K Cutliff
(74) *Attorney, Agent, or Firm* — Sandra B. Weiss

(57) ABSTRACT

The present invention relates to new salts, complexes, crystals, solutions, dispersions, and slurries of threonine-N,N-diacetic acid or derivatives thereof, to formulations containing those, to processes to prepare those, and to the use thereof.

12 Claims, No Drawings

SALTS, CRYSTALS, COMPLEXES, AND DERIVATIVES OF THREONINE DIACETIC ACID, A PROCESS TO PREPARE THREONINE DIACETIC ACID, AND THE USE THEREOF

This application is a national stage filing under 35 U.S.C. §371 of PCT/EP2014/064894, filed Jul. 11, 2014, which claims priority to European Patent Application No. 13176649.5, filed Jul. 16, 2013, the contents of which are each incorporated herein by reference in their entireties.

The present invention relates to new salts, crystals, complexes, and derivatives of the chelating agent threonine-N,N-diacetic acid, to processes to prepare such threonine diacetic acid and its salts, complexes, crystals, and derivatives, and to the use thereof.

The detergent market is currently undergoing important changes. Due to ecological and regulatory reasons the use of phosphate in high concentrations in detergent formulations is to be banned altogether or must at least be greatly reduced. The formulators of detergent products have to find alternatives to replace the phosphate compounds, with the most promising replacements being biodegradable chelating agents. In other areas where acids are used, there is a growing trend towards replacing acids with more eco-friendly materials. In the oil industry operators are also looking for alternatives, and here again biodegradable chelating agents that can be isolated in their acidic form proved to be promising alternatives.

There is a continuous search for new biodegradable chelating agents that are easy to prepare and can be used in the several applications for which chelating agents are used.

One useful, readily biodegradable, chelating agent is serine-N,N-diacetic acid. U.S. Pat. No. 5,019,296 discloses the use thereof in detergents as complexing agent, bleaching agent stabilizer and builder. However, for a chelating agent to be suitable for incorporation in a detergent formulation, the chelating agent should be obtainable in good yield by a simple process with little or no colour.

U.S. Pat. No. 5,019,296 discloses a preparation of serine-N,N-diacetic acid by reacting formaldehyde and hydrogen cyanide with serine and S Korman et al., Journal of Biological Chemistry, Vol. 22, no. 18, 1 Jan. 1956, pp. 113-132 discloses a preparation of serine diacetic acid by reacting serine with monobromo acetic acid, which is from an industrial perspective a less attractive route because of lower yields and expensive raw materials.

When following the process as disclosed in the state of the art, such as the above U.S. Pat. No. 5,019,296 reference, serine-N,N-diacetic acid could only be obtained with a red to brown, sometimes almost black, colour. Such coloured products are highly undesirable, for example when they are used in detergents or in bleaching.

Hence, there is a need in the art to provide alternatives to serine-N,N-diacetic acid or alternative processes that give chelating agents with similar properties but that do not give the same undesired colour, or that do not need additional treatments to remove the colour from the chelating agent.

The present invention now provides processes to prepare threonine N,N-diacetic acid and salts or complexes thereof, provides salts of threonine N,N-diacetic acid of the formula $CH_3—CHOH—C(H)(COOM)-N—(CH_2—COOM)_2$, wherein at least one M is sodium, potassium, lithium, cesium, ammonium, and provides complexes of threonine diacetic acid and a divalent or trivalent cation, wherein the cation is selected from the group of calcium, magnesium, iron, zinc, manganese, aluminum, copper, and cobalt.

Moreover, the present invention covers each of the above products in which the amount of the L-enantiomer (i.e. the 2S, 3R threonine enantiomer; the natural amino acid based enantiomer) is at least 50 mole %, as well as crystals of any of the above products and liquids containing one or more of the above products and a solvent, and dispersions thereof containing a continuous liquid phase.

It should be noted that a number of documents, for instance JP 11021584, JP 2004204055 and WO 2011/154875, mention the compound threonine diacetic acid. However, none of these documents enables the compound in the sense that they clearly and unambiguously demonstrate how to make such compound or where it was acquired. Hence, there is no indication in these documents that the proprietors really had access to the molecule or any derivative thereof that was obtained in the light of the present invention. And what is more, none of the above documents discloses the salts, derivatives, complexes, liquids, solutions or dispersions of threonine diacetic acid or any of its derivatives or their production process or characteristics. In WO 2011/154875 threonine-N,N-diacetic acid is mentioned together with for example the above discussed serine-N,N-diacetic acid, which is, as said, a chelating agent having a not too different chemical structure.

As indicated above, the present invention provides processes to prepare threonine N,N-diacetic acid. The processes of the invention do give the much less coloured to non-coloured chelating agent threonine N,N-diacetic acid and salts thereof, from which also low coloured complexes can be prepared, though it should be realized that some complexes are intrinsically coloured due to the choice of cation, e.g. iron, copper, manganese and cobalt complexes are oftentimes coloured.

The processes of the invention to prepare threonine N,N-diacetic acid are a process comprising two or more steps wherein in one step threonine, a sodium or potassium salt thereof or a mixture thereof is reacted with formaldehyde and hydrogen cyanide, at a pH equal to or below 7, and in another step the nitrile compound formed in the first step is hydrolyzed in the presence of a base, or less preferably in the presence of an acid (a Singer process); a process comprising reacting threonine, a sodium or potassium salt thereof or a mixture thereof with formaldehyde, hydrogen cyanide, a potassium or sodium salt thereof or a mixture thereof, and potassium hydroxide, sodium hydroxide or a mixture thereof, in an aqueous solution, at a pH higher than 7 and at an elevated temperature to remove formed $NH_3$ (a Strecker/Bersworth process); and a process wherein threonine is reacted with a monohaloacetic acid ($CH2X—COOH$, X is a halogen atom, such as chlorine, bromine or iodine) at a temperature between 20 and 80° C., and an alkaline pH to liberate formed HX, giving a threonine-N,N-diacetate salt that may optionally be acidified.

Hence, even though there are similarities between the processes of the state of the art to prepare serine-N,N-diacetic acid and those of the present invention to prepare threonine N,N-diacetic acid, quite unexpectedly the processes of the present invention gave low coloured to non-coloured chelating agent products without performing any colour treatment steps.

The invention in addition relates to the molecule 4-(carboxymethyl)-2-methyl-6-oxomorpholine-3-carboxylic acid, which is basically the molecule of threonine N,N-diacetic acid having undergone a ring closure reaction. This ring closure takes place after subjecting threonine-N,N-diacetic acid to conditions under which water is easily extracted, which are often acidic conditions, such as adding an acid, an ion exchange resin or subjecting the molecule to acidifying electrodialysis, but also increasing the temperature or reducing the pressure, as represented in the scheme below.

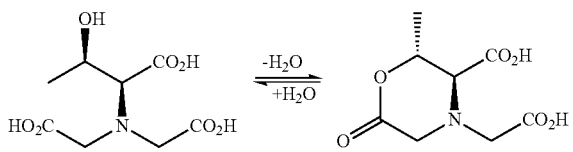

The Formation of Cyclic Ester of THDA Upon Acidification

The fact that threonine-N,N-diacetic acid is capable of ring closing as indicated above makes it a chelating agent with delayed functionality, which is an advantage in many applications where the chelating capacity should take place slowly and not instantaneously, such as the use of the compound in the oil or gas field. It should be noted that threonine N,N-diacetic acid much easier and more completely undergoes the ring closure than serine-N,N-diacetic acid, which is the most similar molecule from a chemical structure perspective, which is another benefit for the products of the present invention.

Moreover, threonine-N,N-diacetic acid can be produced in high yields, forms relatively stable complexes with many cations (to phrase it differently, it is one of the stronger chelating agents within the group of chelating agents that do not bind cations so strongly that they will hardly release them again). Further, the compound is readily biodegradable.

The salts of the invention also cover alkali metal salt of threonine-N,N-diacetic acid (THDA) of the formula $Na_xK_yH_zTHDA$, wherein x and y are more than 0, z is more than and including 0, x and y are up to and including 3, z is lower than 3, and x+y+z=3.

The alkali metal salts wherein y is more than 1 strike a good balance between low viscosity and being obtainable by a process using raw materials that are easily available on an industrial site for a low price. Also, these alkali metal salts have a reasonable molecular weight to viscosity balance, i.e. they have a sufficiently low viscosity to make them transportable and a sufficiently low molecular weight to get sufficient chelate activity per weight unit of alkalimetal chelate salt.

Compared to the full acid of THDA or the trisodium salt of THDA, mixed salts of THDA have the benefit that they can be transported in high concentrations (60% expressed in wt % is no problem) while still having a sufficiently low viscosity to be pumpable at low temperatures (<40° C.). This also means that a smaller amount of material needs to be transported to get the same amount of chelate at the place of destination.

Other advantages of the mixed salt are that the solids content of a mixed THDA salt solution is lower than for a full potassium version for solutions having the same chelating power. The molecular weight of the trisodium salt of THDA, being 301.1, would become 349.5 for the tripotassium salt. So, to get the same active ingredient with respect to sequestering power almost 20% more material would need to be dissolved. The monopotassium disodium THDA of the invention requires only 5% more product to be dissolved instead of 20%, and this without the product having the negative effect of high viscosity at more concentrated solutions when compared with the trisodium version.

Preferably, in the alkali metal salt of THDA of the invention x is between 1.5 and 2.5 and y is between 0.5 and 1.5, most preferably x is about 2 and y is about 1.

In one embodiment the invention provides a process to prepare the above (alkali metal salts of) threonine-N,N-diacetic acid (THDA) comprising reacting threonine, a sodium or potassium salt thereof or a mixture thereof, with formaldehyde, hydrogen cyanide, a potassium or sodium salt thereof or a mixture thereof, and potassium hydroxide, sodium hydroxide or a mixture thereof, in an aqueous solution at an elevated temperature to remove formed $NH_3$.

In an embodiment during the process the molar ratio of sodium to potassium in the reactants is between 1:1 and 5:1. Preferably, the molar ratio of sodium to potassium in the reactants is between 1:1 and 3:1, most preferably about 2:1.

In this embodiment the novel threonine-N,N-diacetic acid salt is prepared by a so-called Strecker/Bersworth route at alkaline conditions using an 1-pot synthesis. The reaction route encompasses reacting threonine with formaldehyde and hydrogen cyanide in the presence of sodium hydroxide and potassium hydroxide. The excess cyanide/formaldehyde needed is 10% or more; use is made of a minimum of 2.2 equivalents cyanide/formaldehyde per equivalent of threonine.

The individual dosing of formaldehyde and HCN can also be combined to generate glycolonitrile ($HO-CH_2-CN$). This glycolonitrile is reacted with threonine or the sodium or potassium salt thereof in an alkaline environment (Strecker/Bersworth process).

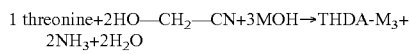

1 threonine+2HO—$CH_2$—CN+3MOH→THDA-$M_3$+2$NH_3$+2$H_2O$

Preferably, the threonine diacetic acid and its (alkali metal) salts of the invention are prepared by a Singer process comprising two or more steps, wherein in a first step threonine, a sodium or potassium salt thereof or a mixture thereof is reacted with formaldehyde and hydrogen cyanide at a pH equal to or below 7, and in a subsequent step the nitrile compound formed in the first step is hydrolyzed with an alkali metal hydroxide, and optionally acidified in a next step.

The acidification step can be performed by adding an organic or inorganic acid, but is preferably done, mainly to avoid the formation of salt, by reaction with an ion exchange resin or by an electrodialytical acidification, such as for example disclosed in EP-A-1004571 or EP-A-2086923.

In a preferred embodiment a mixture of alkali metal hydroxides can be used, for example one wherein the molar ratio of sodium to potassium in the reactants is between 1:1 and 5:1.

In a more preferred embodiment, a two-step process in which the first step takes place at neutral or acidic pH (the above so-called Singer process), between 1.6 and 2.4 equivalents of formaldehyde are used per equivalent of threonine or salt thereof and 1.6 to 2.4 equivalents of HCN are used per equivalent of threonine or salt thereof. In an even more preferred embodiment, 1.9-2.1 equivalents of formaldehyde and HCN are used per equivalent of threonine or salt thereof. Most preferably, the amount of formaldehyde and HCN is about 2.0 equivalents per equivalent of threonine or salt thereof. In the process the amount of HCN may be (but does not need to be) the same as the amount of formaldehyde.

For very low NTA levels the two-step Singer process is preferred over the Strecker process.

The overall reaction is:

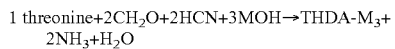

1 threonine+2$CH_2O$+2HCN+3MOH→THDA-$M_3$+2$NH_3$+$H_2O$

It will be clear that instead of starting with threonine, it is possible to use the sodium or potassium salt of threonine. The same holds for hydrogen cyanide; sodium cyanide and potassium cyanide are alternatives. Potassium hydroxide can be used instead of sodium hydroxide.

In a more preferred embodiment, the first step is split up into two substeps, firstly a reaction of threonine or its salt with formaldehyde to generate a Schiff base intermediate and subsequently a reaction with HCN and remaining formaldehyde to form threonine N,N diacetonitrile.

In the above preferred process the raw material is monosodium salt of threonine, threonine or the monopotassium salt of threonine. The solubility of threonine can be enhanced by dissolving it in MOH (resulting in the formation of monosodium or monopotassium salt); having about 0.6-1.4 equivalents of base is preferred. In the manufacturing of THDA the monosodium salt or monopotassium salt of threonine is then dissolved in water and formaldehyde and cyanide are added to obtain final reaction mixture with acidic or neutral pH.

In the case of synthesis of the intermediate nitrile the addition of formaldehyde and hydrogen cyanide preferably takes place at a temperature between 0 and 70° C., preferably 0 and 40° C. The result is an intermediate product having two nitrile functionalities. These types of products are known as aminoacetonitriles or, for short, "nitriles". The nitrile of THDA, e.g. threonine-N,N-diacetonitrile, is also indicated as THDN below. The nitrile, being a water-soluble compound, is hydrolyzed in a second step applying caustic.

The overall reaction will be:

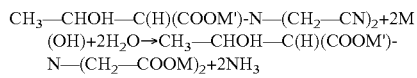

(aminoacetonitrile intermediate+base→aminocarboxylate+ammonia)

In the above reaction each M and M' may be the same or different and represent an alkali metal ion.

The process has as an additional benefit that having potassium THDN one needs only sodium hydroxide to produce the THDA-KNa2. Not all production locations have access to KOH or storage tanks of KOH; NaOH is more commonly used. Production of a mixed salt is easier than of the full potassium version that requires KOH to be present in each location, i.e. the location carrying out the nitrile hydrolysis only needs the commonly used NaOH.

Accordingly, a process is provided wherein in the first step the threonine diacetonitrile monopotassium salt is formed by reacting either potassium salt of threonine with hydrogen cyanide and formaldehyde or threonine with potassium cyanide and formaldehyde, the nitrile being hydrolyzed with sodium hydroxide in the subsequent step.

As starting material instead of threonine also the potassium salt thereof can be employed. The main advantage of monopotassium salt of threonine in the production process is its very high solubility even at room temperature. Monosodium threonine has a high solubility in water at room temperature (higher solubility compared to the non-salt threonine itself), monopotassium threonine has an even higher solubility. The more concentrated the threonine can be processed, the less water removal is required to make a concentrated THDA solution. The monosodium THDN (=threonine diacetonitrile monosodium salt) manufactured has a concentration related to the maximum achievable concentration of the monosodium salt of threonine and the amount of water added by using aqueous formaldehyde. It will be clear that the use of concentrated formaldehyde solutions is advantageous.

In the case of the potassium version of THDN, the final nitrile concentration will be higher due to the higher solubility of potassium salt of threonine. It allows for more economical transport, more output per reactor volume, lower energy costs, and is an easy way to produce highly concentrated final THDA solutions in the hydrolysis of the nitrile functionalities without water removal.

To be able to make specific $Na_xK_yH_zTHDA$ salts of the invention, a process wherein the ratio between x and y can be easily fine-tuned is also desired.

Therefore the invention provides the following two alternative processes. Firstly, a process comprising titrating threonine-N,N-diacetic acid (or an appropriate derivative or salt thereof) with a sodium salt and a potassium salt wherein the molar ratio of sodium to potassium in the materials is between 5:1 and 1:1 and, secondly, a process of mixing the trisodium salt of THDA and the tripotassium salt of THDA in a molar ratio of between 5:1 and 1:1.

The complexes of the present invention are made by contacting a salt of threonine diacetic acid or the acidic version of threonine diacetic acid with a compound containing a divalent or trivalent metal cation, like a salt of such a metal cation, preferably, the carbonate, oxide or hydroxide salt of such cation to avoid the formation of further salts, even more preferably the oxide salt, as hydroxide salts sometimes are not too soluble and the use of carbonate salts may result in the formation of a considerable amount of $CO_2$ gas, which is sometimes undesirable. When using a metal oxide, it is preferred to use the threonine N—N-diacetic acid in the acidic version. The complexes are normally made in a solvent, preferably water.

The ammonium salts of the present invention are preferably made by contacting the acidic version of threonine diacetic acid (i.e. wherein at least one of the counterions is a hydrogen ion) with an ammonium salt or ammonia, preferably with $NH_4OH$.

Finally, the present invention relates to the use of the alkali metal salts in a detergent or bleaching composition, a descaling composition, a microbial composition, human food or animal feed composition, an oil or gas well treatment composition, a micronutrient composition, in gas sweetening, pulp and paper bleaching, drilling, or in the preparation of any of such compositions.

EXAMPLES

Example 1

The Synthesis of Trisodium Threonine Diacetate Using Sodium Cyanide

A 1 liter reactor was charged with 178.5 g threonine, (1.5 moles), 300 g water, and 130 g 50 wt % aqueous NaOH (1.6 moles). The reactor contents were heated to boiling temperature. Simultaneously in circa 3 hours 4.0 moles sodium cyanide solution (30 wt %) and 4.0 moles formaldehyde solution (44 wt %) were dosed. After the dosing was completed 2 hrs of boiling off ammonia/water took place (level control of the mixture by addition of water).

Circa 995 grams of a light-coloured solution having a Fe-sequestering capacity of 48 wt % were obtained, which contained <1 wt % of the starting material, threonine, indicating a good conversion.

$^{13}C$ and $^1H$ NMR showed threonine diacetate formation.

Example 2

The Synthesis of Trisodium Threonine Diacetate Using HCN

A 1 liter reactor equipped with a stirrer, thermometer, and pH meter was charged with 104 g threonine (0.87 moles), 500 g water, and 5.5 grams 50 wt % aqueous NaOH. To this solution 67 g 44.3% formaldehyde solution (0.99 moles) were added. Subsequently over a period of 80 minutes, 54 g HCN (2.00) moles and 67 g (0.99 moles) 44.3 wt % formaldehyde were co-dosed. The pH was adjusted to 4 with 50% sodium hydroxide. The threonine diacetonitrile solution was dosed over a period of 90 minutes to a reactor that contained 209 g 50% caustic and 250 g water. After dosing had been completed the ammonia was boiled off by evaporating water/ammonia at 109° C. using level control by addition of water. The reactor mixture (650 grams) showed a Fe-sequestering capacity of 28%.

$^1$H and $^{13}$C NMR analysis was used to prove that threonine diacetate was formed.

Example 3

The Synthesis of Trisodium Threonine Diacetate Using Monochloroacetic Acid

A 3 liter jacketed reactor with baffles and turbine stirrer was charged with 858 g of water and 361.0 g (3 moles) of L-threonine (99%, Fluka). This slurry is heated to 60° C. The dosing of 50 wt % aqueous NaOH solution was started and the pH value was maintained at 8.0 during the process when dosing a 42.9 wt % aqueous solution of sodium monochloroacetate. The reaction was monitored by the determination of its sequestering value.

A constant sequestering value having been reached, a total of 2,584.4 g (9.52 moles) of a 42.9% aqueous solution of sodium monochloroacetate and 788 g (9.85 moles) of a 50% aqueous NaOH solution was dosed altogether.

The formation of the desired product could be proven by NMR- and CZE-analytical techniques.

Example 4

The Synthesis of Threonine Diacetic Acid

The solution obtained in example 1 was acidified using an ion exchange resin. Acidification took place using Amberlite IR-120, a strong acid ion exchange resin: 55 g of GLDA solution, 110 g of Amberlite IR-120 as such, and ca 100 g of water were stirred in a 500 ml round-bottomed flask for at least 48 h. After filtering off the resin the solution was dried by evaporation of water at reduced pressure at 70° C. The light-coloured crispy foam obtained was further dried in a vacuum oven at 65° C. This resulted in a solid product in a yield of circa 85%.

NMR and FT-IR showed THDA:THDA$_{ring\ closed}$ in a weight ratio of 90:10. This means that the THDA acid was formed but during the formation part of it cyclized and this created the product as further described in Example 5 below.

Example 5

The synthesis of (2R,3S)-4-(carboxymethyl)-2-methyl-6-oxomorpholine-3-carboxylic acid The ratio of open/closed structure in solution is dependent on a number of factors such as e.g. pH-value, concentration. The ratio of open/closed structure in solid form strongly depends on factors like e.g. drying time, temperature, strength of vacuum applied.

The product obtained in Example 4 was dried for 1 month at 40° C.; this resulted in a solid product having a ratio THDA:THDA$_{ring\ closed}$=10:90 proven by NMR and FT-IR.

Example 6

Acidification with Concentrated Hydrochloric Acid

To 25 g of the solution of Example 1 (pH=13.3) in a 250 ml round-bottomed flask carefully concentrated HCl was added dropwise. Water and surplus HCl were removed with a rotavap under reduced pressure at 100° C. until a crispy (crystalline) foam remained. This material was dried further in the 250 ml round-bottomed flask in a vacuum oven at 100° C. for 48 h.

NMR and FT-IR showed the THDA:THDA$_{ring\ closed}$ ratio of 60:40.

Example 7

Acidification with Glacial Acetic Acid

Water was removed from 50.8 g of the solution of Example 1 using a rotavap at 65° C. under reduced pressure. This resulted in 39.41 g of solid material. After dissolving this solid in glacial acetic acid (100 ml) the solution was precipitated by mixing with about 1,200 ml of isopropyl alcohol (IPA). After filtration through a G2 filter frit the solid was dried in a vacuum oven under reduced pressure at 100° C., resulting in 15.49 g of colourless material with a THDA:THDA$_{ring\ closed}$ ratio of 80:20

Example 8

The Synthesis of Threonine Diacetate Solid

The solution obtained in Example 1 was used to prepare the powder of threonine diacetate.

In spite of the hygroscopic nature of THDA-Na$_3$ solid, the solution was easy to spray-dry using an inlet air temperature of 200° C. and tuning the outlet temperature at 115° C. by the flow rate. A free flowing crystalline white powder was obtained. The moisture content of ca. 7% was determined by Karl Fisher titration.

Example 9

The Synthesis of Calcium Complex of Threonine

The pH of 37.8 wt % aqueous solution of THDA-Na$_3$ was adjusted to pH=6 by addition of 37 wt % aqueous HCl. To the obtained mixture an equimolar amount of an aqueous solution of CaCl$_2$.2H$_2$O was added, followed by partial evaporation under vacuum to give a concentrated mixture. The concentrated mixture was left standing overnight at room temperature for further crystallization. The obtained solids were filtered off, washed with water (3×1 ml), and dried under vacuum (50° C.) to obtain white crystals. The formation of the crystalline Ca-THDA complex was supported by XRD, ICP, ESI-MS, and NMR analysis of the isolated material.

Example 10

The Synthesis of Iron (III) Complex of Threonine Diacetate 33.4 wt % THDA.Na$_3$ (2 g, 2.2 mM; prepared by adjusting pH of 38 wt % THDA.Na$_3$ to 7 with 70 wt % HClO$_4$) was added to a solution of Fe(ClO$_4$)$_3$.xH$_2$O (1.242 g, 2.2 mM, determined by potentiometric titration) in water (0.62 ml). Water (0.95 g) was partially evaporated from the reaction mixture under vacuum to give a yellow-brown transparent viscous solution. The concentrated solution was left to crystallize at ambient temperature for 2 h. The solids were filtered off, washed with water (0.5 ml), and dried under vacuum (50° C.) to obtain 0.681 g of a yellow crystalline powder. The iron complex formation was supported by XRD, ICP and NMR data.

Example 11

The Synthesis of Zinc Complex of Threonine Diacetate

The pH of 37.8 wt % aqueous solution of THDA-Na$_3$ (10 g, 12.7 mM) was adjusted to pH=7 by addition of 37 wt % aqueous HCl. To the obtained mixture a solution of ZnCl$_2$ (1.719 g, 12.7 mM) in water (3.0 g) was added, followed by partial evaporation under vacuum to give 11.8 g of concentrated mixture containing white solids. The solids were filtered off, washed with water (3.4 ml), and dried under vacuum (50° C.) to obtain 2.34 g of white crystals. The formation of the crystalline Zn-THDA complex was supported by XRD, ICP, ESI-MS, and NMR analysis of the isolated material.

Example 12

The Synthesis of Copper(II) Complex of Threonine Diacetate

A 34.3 wt % solution of THDA.Na$_3$ in water (2 g, 2.3 mM; prepared by adjusting pH of 38 wt % THDA.Na$_3$ to 7 with 37 wt % HCl) was added to a solution of anhydrous CuCl$_2$ (0.306 g, 2.3 mM) in water (1 ml). The resulting blue homogeneous solution was partially evaporated (1.42 g of water was removed) under vacuum and left at ambient temperature for crystallization. After 5 days at room temperature the crystals were filtered off, washed with water (0.5 ml), and dried under vacuum (50° C.) to obtain 0.37 g of blue crystals. The formation of the expected crystalline Cu-THDA complex was supported by XRD, ICP, ESI-MS, and NMR analysis of the isolated material.

Example 13

Use of THDA in Several Applications to Sequester Calcium or Iron a) Use of THDA for Dissolving Insoluble Calcium Salts A mixture of CaCO$_3$ (1.26 g, 12.6 mM), 37.8 wt % THDA.Na$_3$ in water (15 g, 18.8 mM), and water (45 g) was vigorously stirred for 6 h. The experiment was performed at room temperature and at 50° C. Samples (1 ml) were taken from the mixture every 0.5 h and filtered through a 0.45 μm filter. The concentration of calcium in the filtered samples was determined using the ICP method. It was shown that a significant amount of CaCO$_3$ could be dissolved. The dissolution occurred noticeably faster at 50° C.

b) Use of THDA for Sequestering Fe(III) at Low and High pH.

Potentiometric titration of THDA with FeCl$_3$ at pH 3-4 and 11.5 gave the iron total sequestering values (Fe-TSV) of 37.8 and 27.8%, respectively. This demonstrated that even at high pH a significant amount of Fe(III) is bound by the chelating agent. All Fe(III) is bound by THDA at pH 3-4.

Comparative Example 14

Preparation of serine-N,N-diacetic acid using sodium cyanide

Following the procedure as in Example 1, a 1 liter reactor was charged with 157.6 g serine, (1.5 moles), 120 g water, and 123 g 50 wt % aqueous NaOH (1.54 moles). The reactor contents were heated to boiling temperature. Simultaneously in circa 3 hours 4.0 moles sodium cyanide solution (30 wt %) and 4.0 moles formaldehyde solution (44 wt %) were dosed. After the dosing was completed 2 hrs of boiling off ammonia/water took place (level control of the mixture by addition of water). Ca. 1080 grams of a black-brown solution having a Fe-sequestering capacity of 40 wt % were obtained, which contained <1 wt % of the starting material, serine, indicating a good conversion. $^{13}$C and $^1$H NMR showed serine diacetate formation.

Example 15

Cyclisation of threonine diacetic acid to (2R,3S)-4-(carboxymethyl)-2-methyl-6-oxomorpholine-3-carboxylic acid A 30% aqueous solution of disodium threonine diacetate (129 mg) was mixed well with a DMSO-d$_6$/TFA solution (2761 mg, 80:20 w/w) and changes in the obtained mixture were monitored by $^1$H NMR at ambient temperature. The steady state was reached after 40 minutes with a conversion of 90% of THDA to cyclic-THDA.

Comparative Example 16

Cyclisation of serine diacetic acid to (S)-4-(carboxymethyl)-6-oxomorpholine-3-carboxylic acid A 30% aqueous solution of disodium serine diacetate (136 mg) was mixed well with a DMSO-d$_6$/TFA solution (2911 mg, 80:20 w/w) and changes in the obtained mixture were monitored by $^1$H NMR at ambient temperature. The steady state was reached after 100 minutes with a conversion of 43% of SerDA to cyclic-SerDA. The above experiments support that THDA can be used in applications that relate to dissolving carbonate or sequestering iron, such as use in the oil field (e.g. dissolving CaCO$_3$ and controlling iron in subterranean treatment), use in a feed, food or micronutrient composition (e.g. complexing iron and calcium for delivery to growing substrates), use in detergents and water treatments (e.g. sequestering calcium from water to soften water and sequestering iron present in stains), and many more uses.

The invention claimed is:

1. A process to prepare threonine-N,N-diacetic acid or a salt thereof comprising two or more steps wherein in a first step threonine, a sodium or potassium salt thereof or a mixture thereof is reacted with formaldehyde and hydrogen cyanide, at a pH equal to or below 7 to form a nitrile compound, and in a second step the nitrile compound formed in the first step is hydrolyzed by the addition of an acid or base.

2. A process to prepare threonine-N,N-diacetic acid or a salt thereof comprising reacting threonine, a sodium or potassium salt thereof or a mixture thereof with formaldehyde, hydrogen cyanide, a potassium or sodium salt thereof or a mixture thereof, and potassium hydroxide, sodium hydroxide or a mixture thereof, in an aqueous solution at an alkaline pH and at an elevated temperature to remove formed NH$_3$.

3. A process to prepare threonine-N,N-diacetic acid or a salt thereof, wherein threonine is reacted with a monohaloacetic acid at a temperature of 20 to 80° C. and an alkaline pH.

4. The process of claim 1 wherein said nitrile compound is threonine-N,N-diacetonitrile or a salt thereof.

5. The process of claim 1 wherein subsequent to the hydrolysis step an acidification step is performed.

6. The process of claim 2 wherein subsequent to the reaction at alkaline pH an acidification step is performed.

7. The process of claim 3 wherein said monohaloacetic acid is monochloroacetic acid.

8. The process of claim 3 wherein the reaction product is a salt of threonine-N,N-diacetic acid and a subsequent acidification step is performed to convert the salt formed into the acid.

9. A composition comprising a compound selected from the group consisting of
- a complex of threonine-N,N-diacetic acid and a divalent or trivalent cation, wherein the cation is selected from the group of calcium, magnesium, iron, zinc, manganese, aluminium, copper, and cobalt; and
- a salt of threonine-N,N-diacetic acid of the formula $CH_3$—$CHOH$—$C(H)(COOM)$-$N$—$(CH_2$—$COOM)_2$, wherein at least one M is chosen from the group of sodium, potassium, lithium, cesium, and ammonium.

10. The composition of claim 9 wherein said compound is in crystalline form.

11. The composition of claim 9 wherein said composition is a formulation comprising a liquid.

12. The composition of claim 11 wherein the liquid is water.

* * * * *